US008511638B2

(12) United States Patent  (10) Patent No.: US 8,511,638 B2
Mansour et al.  (45) Date of Patent: Aug. 20, 2013

(54) NEONATAL LUER-ACTIVATED MEDICAL CONNECTOR

(75) Inventors: George Michel Mansour, Pomona, CA (US); Tyler Devin Panian, Long Beach, CA (US)

(73) Assignee: CareFusion 303, Inc., San Diego, CA (US)

( * ) Notice: Subject to any disclaimer, the term of this patent is extended or adjusted under 35 U.S.C. 154(b) by 230 days.

(21) Appl. No.: 13/016,883

(22) Filed: Jan. 28, 2011

(65) Prior Publication Data

US 2011/0130724 A1    Jun. 2, 2011

Related U.S. Application Data

(63) Continuation-in-part of application No. 12/204,941, filed on Sep. 5, 2008, now Pat. No. 8,074,964.

(51) Int. Cl.
*F16L 37/28*   (2006.01)
*F16L 29/00*   (2006.01)
*F16K 51/00*   (2006.01)

(52) U.S. Cl.
USPC ................................. 251/149.6; 251/149.3

(58) Field of Classification Search
USPC ................. 251/149.1, 149.3, 149.6, 149.7
See application file for complete search history.

(56) References Cited

U.S. PATENT DOCUMENTS

| 4,683,916 A | 8/1987 | Raines |
| 5,360,413 A | 11/1994 | Leason et al. |
| 5,569,235 A | 10/1996 | Ross et al. |
| 5,578,059 A | 11/1996 | Patzer |
| 5,730,418 A | 3/1998 | Feith et al. |
| 5,806,831 A * | 9/1998 | Paradis ....................... 251/149.1 |
| 6,089,541 A * | 7/2000 | Weinheimer et al. ....... 251/149.6 |
| 6,158,458 A | 12/2000 | Ryan |
| 6,482,188 B1 * | 11/2002 | Rogers et al. ................. 604/249 |
| 2003/0183795 A1 * | 10/2003 | Doyle ......................... 251/149.1 |

(Continued)

FOREIGN PATENT DOCUMENTS

| DE | 4311715 A1 | 10/1994 |
| EP | 0471547 A1 | 2/1992 |
| WO | 2006062912 A1 | 6/2006 |

OTHER PUBLICATIONS

International Search Report and Written Opinion issued for PCT/US2009/055732, dated Nov. 13, 2009, in 7 pages.

(Continued)

*Primary Examiner* — John K Fristoe, Jr.
*Assistant Examiner* — Frederick D Soski
(74) *Attorney, Agent, or Firm* — McDermott Will & Emery LLP

(57) ABSTRACT

A connector is disclosed that has a housing having a fluid path from a first port through an internal cavity to a second port. The connector also includes a plug that has first and second positions within the internal cavity, where the plug blocks the fluid path between the first port and the internal cavity when in the first position. The plug has a diaphragm that separates the internal cavity into a first volume that is vented and a second volume that includes the fluid path. The plug also includes a biasing element that is disposed within the first volume and that urges the plug toward the first position. Displacement of the plug from the first position toward the second position opens the fluid path and increases the second volume.

9 Claims, 11 Drawing Sheets

(56) References Cited

U.S. PATENT DOCUMENTS

| | | |
|---|---|---|
| 2004/0158210 A1 | 8/2004 | Staunton et al. |
| 2005/0006614 A1* | 1/2005 | Leinsing et al. ............ 251/149.6 |
| 2006/0108555 A1* | 5/2006 | Kiehne ....................... 251/149.7 |
| 2007/0007478 A1* | 1/2007 | Leinsing et al. ............ 251/149.1 |
| 2008/0087859 A1* | 4/2008 | Enerson et al. ............. 251/149.7 |
| 2008/0103482 A1 | 5/2008 | Fangrow |
| 2008/0169444 A1 | 7/2008 | Guala |
| 2008/0215014 A1 | 9/2008 | Nordgren |
| 2010/0059702 A1 | 3/2010 | Mansour et al. |

OTHER PUBLICATIONS

Supplementary European Search Report for EP 09 81 2166 dated Aug. 11, 2011, in 6 pages.

International Search Report and Written Opinion for PCT/US2012/023028, mailed Aug. 24, 2012.

* cited by examiner ved connectors which don't require hypodermic needles, but instead use an activator such as a Luer on the end of a syringe or intravenous (IV) line to create a fluid path through a valve in a connector. The removal of the connector causes the valve to close when the line is disconnected. Such a system is described in U.S. Pat. No. 5,569,235 to Ross et al, for example.

NEONATAL LUER-ACTIVATED MEDICAL CONNECTOR

This application is a continuation-in-part of application Ser. No. 12/204,941 filed on Sep. 5, 2008, now pending.

BACKGROUND

1. Field

The present disclosure generally relates to medical connectors used in fluid delivery applications, and more specifically to connectors having a low priming volume and low positive displacement on disconnection.

2. Description of the Related Art

Medical connections are widely used in fluid delivery systems such as those used in connection with intravenous fluid lines, blood access, hemodialysis, peritoneal dialysis, enteral feeding, drug vial access, etc. Many prior art aseptic medical connectors employ an arrangement to puncture an elastomeric diaphragm or septum, which has one side in contact with the fluid, with a sharpened hollow hypodermic needle. The use of such hypodermic needles has been gradually decreasing as a result of both safety and cost considerations associated with infectious disease acquired from needle sticks. These connectors have been replaced with Luer acti- Typical connectors and valves of this type, such as described by Ross, have many attributes that are not ideal in medical applications for fluid delivery. First, such devices can have large priming volumes, that is the connector can have a large chamber associated with the valve element that must be filled with the fluid being delivered before that fluid is actually delivered into the patient line and the patient. For very low flow rates (for example, 0.1 milliliter per hour or 0.05 milliliters per hour), as is common for neonatal or infant care as well as other types of care, such a large priming volume can cause a delay of as much as several hours before the intended therapy reaches the patient.

Second, fluid displacement can occur whenever a connection is made between two closed fluid systems. When a connection, such as a Luer or hypodermic needle, is inserted into an intravenous connector or fluid tubing, fluid displacement occurs. Because the intravenous fluid is incompressible, a volume of fluid equal to the Luer or needle volume is displaced out of the intravenous tubing and into the patient's blood vessel. This displacement of fluid from the intravenous tubing into the patient's blood vessel is referred to as antegrade flow. Similarly, when the connection is withdrawn, an equivalent volume of blood will be drawn back, usually through the catheter, into the intravenous tubing. This retrograde flow can be harmful when the blood drawn into the end of the catheter remains stagnant for a long period of time. The stagnant blood tends to settle, and may begin to clot, thereby restricting flow through the catheter and possibly requiring insertion of a new intravenous catheter into the patient. Connector systems providing for negative, or retrograde, displacement on insertion and positive, or antegrade flow on removal, are much more desirable in medical applications.

Third, most connectors use a septum, or permeable membrane at the connection site. These membranes must be penetrated on the insertion of the connector and therefore promote bacteria growth inside the connector. This septum is also susceptible to leaking when there is back pressure in the system. Connector systems that have swabbable surfaces to allow for cleaning and that prevent leakage under backpressure are preferable.

SUMMARY

A connector having a low priming volume would allow an introduced therapy to reach the patient more quickly, even at low flow rates.

An embodiment of a connector is described having a valve housing defining an inlet port, and an outlet port, the valve housing further including a fluid path from the inlet port to the outlet port. The connector further includes a valve plug operable to seal the inlet port when the connector is in an unactuated state thereby closing the fluid path through the connector, and a diaphragm in the valve housing, the diaphragm separating the valve plug from an inner volume in the valve housing and the diaphragm sealing the inner volume, such that upon actuation of the connector the valve plug deforms the diaphragm into the inner volume thereby unsealing the inlet port and opening the fluid path through the connector.

A embodiment of a method of operating a connector for medical fluids is also described. The method includes actuating the connector by depressing a valve plug in the connector by inserting a male luer into an inlet port of the connector, the depressing of the valve plug opening a fluid path through the connector, deforming a diaphragm under pressure from the valve plug, the diaphragm defining and sealing an inner volume inside a valve housing of the connector, wherein the deformation of the diaphragm causes the connector to exhibit negative fluid displacement upon actuation, and closing the connector by removing the male Luer from the inlet port, wherein the removal of the male Luer causes the valve plug to reseal the connector and the diaphragm to return to an undeformed state, wherein the return of the diaphragm to the undeformed state causes the connector to exhibit positive fluid displacement upon disconnection.

In another embodiment of the connector described herein, the connector includes a valve housing having a valve housing base and a valve cap, the valve housing defining an inlet port, and an outlet port, the valve housing further including a fluid path from the inlet port to the outlet port, the fluid path including a channel formed in an inner wall of the valve housing. The connector also includes a valve insert in the valve housing, the valve insert defining a bowl and a diaphragm in the valve housing and sealing the bowl of the valve insert, the sealed bowl forming an inner volume in the valve housing. A valve plug is operable to seal the inlet port when the connector is in an unactuated state thereby closing the fluid path through the connector, and wherein the diaphragm contacts the valve plug and applies a force to the valve plug to maintain the valve plug in the unactuated state. Upon actuation of the connector the valve plug deforms the diaphragm into the inner volume thereby unsealing the inlet port and opening the fluid path through the connector.

In another embodiment of the connector described herein, the connector includes a housing having an internal cavity with first and second ports and a fluid path from the first port through the internal cavity to the second port. The connector also includes a plug having first and second positions within the internal cavity. The plug is configured to block the fluid path between the first port and the internal cavity when in the first position. The plug comprises a diaphragm configured to separate the internal cavity into a first volume that is vented and a second volume that includes the fluid path, and a biasing element disposed within the first volume, the biasing element configured to urge the plug toward the first position. Displacement of the plug from the first position toward the second position opens the fluid path and increases the second volume.

Certain embodiments described herein comprise a medical device that comprises a connector that includes a housing having an internal cavity with first and second ports and a fluid path from the first port through the internal cavity to the second port. The connector also includes a plug having first and second positions within the internal cavity. The plug is configured to block the fluid path between the first port and the internal cavity when in the first position. The plug comprises a diaphragm configured to separate the internal cavity into a first volume that is vented and a second volume that includes the fluid path, and a biasing element disposed within the first volume, the biasing element configured to urge the plug toward the first position. Displacement of the plug from the first position toward the second position opens the fluid path and increases the second volume.

Certain embodiments described herein comprise a connector having a housing having an internal cavity with first and second ports, with a flow path from the first port through the internal cavity to the second port. The connector also includes an insert having a bowl with the insert disposed within the internal cavity of the housing. The connector also includes a resilient valve that is partially disposed within the bowl, the valve also having a diaphragm sealed to the edge of the bowl, forming a sealed air space with the bowl. The connector also includes a vent path from the air space through the insert that is coupled to a vent path from the internal cavity through the housing to the external environment.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

According to the concepts described herein, a needleless access medical device that combines a low priming volume, positive displacement disconnection, and a swabbable surface for disinfecting between uses is described.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

The method and system disclosed herein are presented in terms of a connector adapted for use is delivering medical fluid to a patient, particularly an infant. It will be apparent to those of ordinary skill in the art that the disclosed concepts may be applied to a variety of applications where these same features of a low priming volume, positive displacement disconnection, and a swabbable surface for disinfecting between uses are of value. Nothing in this disclosure should be interpreted, unless specifically stated as such, to limit the application of any method or system disclosed herein to neonatal medical applications.

According to the concepts described herein, a needleless access medical device that combines a low priming volume, positive displacement disconnection, and a swabbable surface for disinfecting between uses is described.

Figure 1:
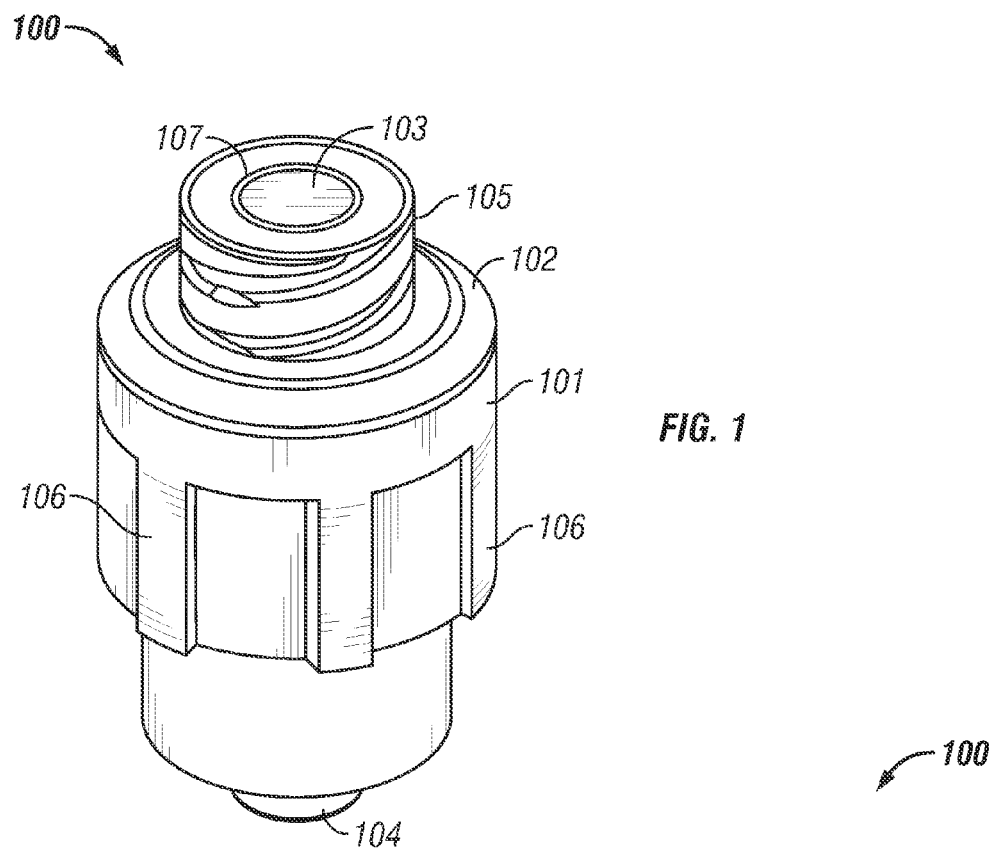
FIG. 1 is a perspective view of a Luer activated medical connector in accordance with the concepts described herein.
Figure 2:
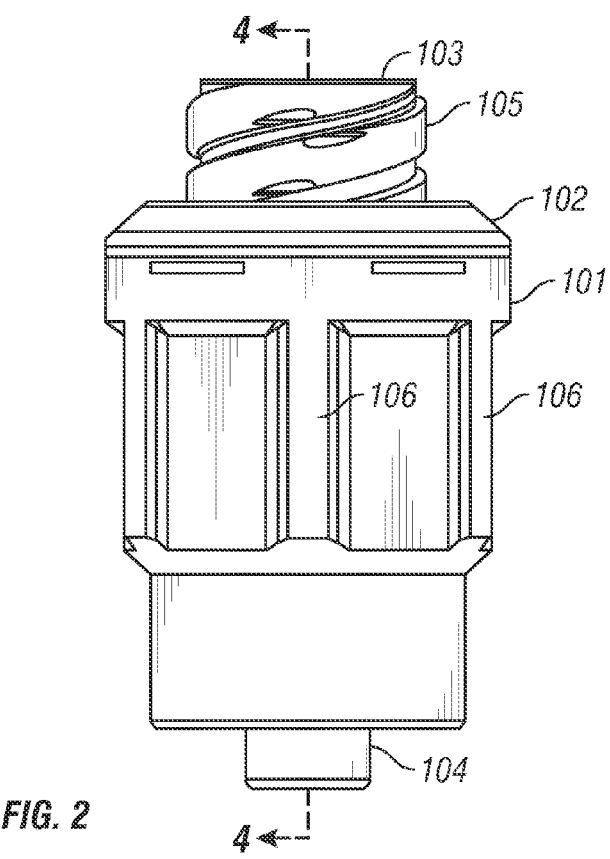
FIG. 2 is a side view of the medical connector shown in FIG. 1.

Turning to FIGS. 1 and 2, an embodiment of a low priming volume Luer activated connector 100 according to the concepts described herein is shown in perspective view and side view respectively. The Luer activated connector 100 is formed by valve housing 101 and a valve cap 102. Valve cap 102 is secured to the valve housing 101 using conventional means, such as solvent bonding, ultrasonic, spin welding, etc. A valve inlet port 103 is sealed by the top of valve plug 107 which forms a swabbable surface that can be cleaned between uses. Valve inlet port 103 accepts an actuator that pushes valve plug 107 into valve housing 101 to create a fluid path through connector 100 as will be described below. Valve inlet port 103 includes threads that allow connector 100 to be securely connected to a syringe or other fluid dispensing mechanism.

Housing ribs 106 provide structural support to valve housing 101 and also provide for gripping surfaces to allow connector 100 to be held firmly while attaching another device. As will be described below, in certain disclosed embodiments, a channel is formed on the interior of one of the ribs that provides a low priming volume fluid path through connector 100. Actuator 104 allows the connector to be connected to the inlet port of another device, such as an IV tube or manifold.

Figure 3:
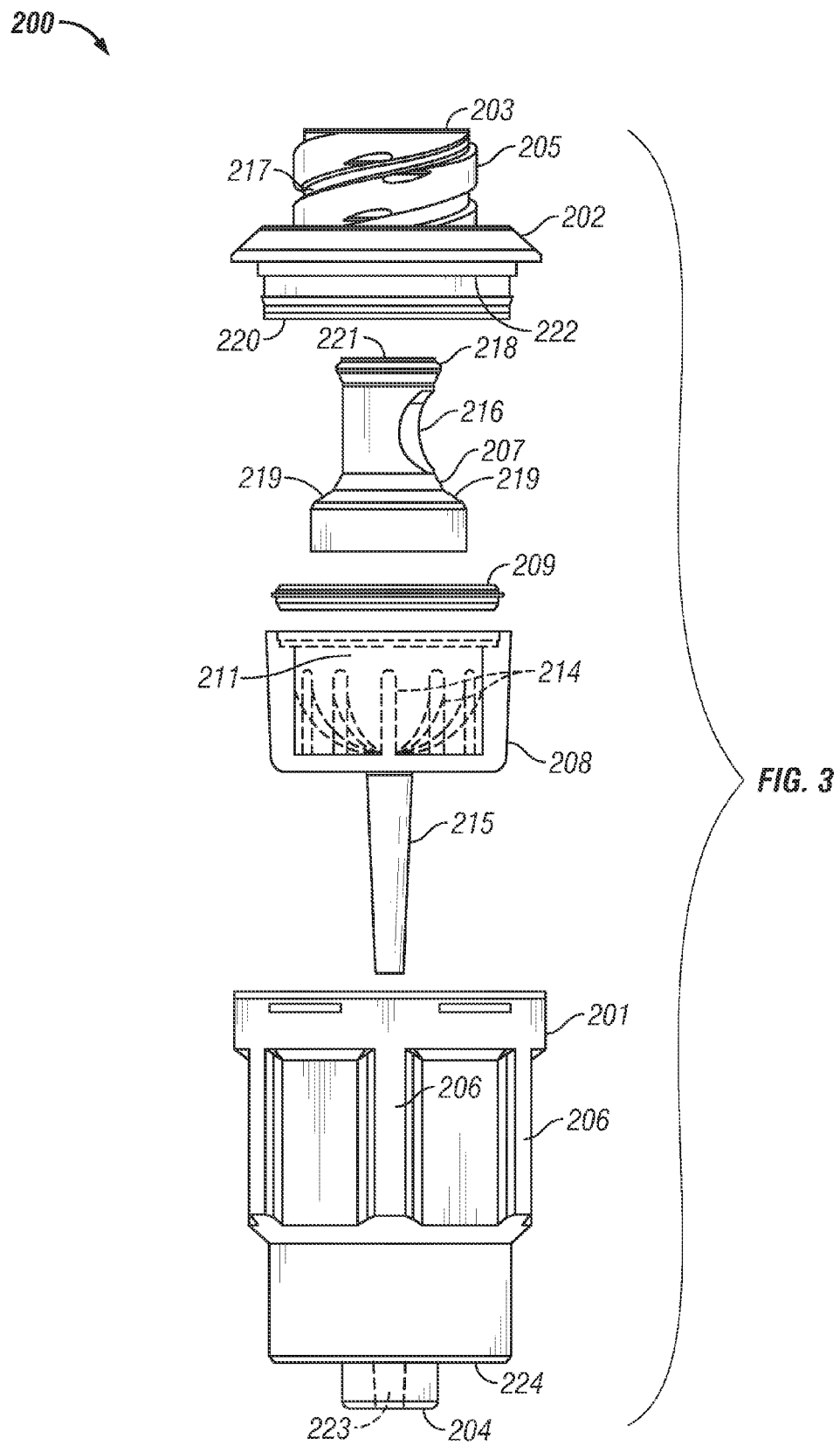
FIG. 3 is an exploded side view of the medical connector shown in FIG. 2.

Referring now to FIG. 3, an embodiment of connector 200 according to the concepts described herein is shown in an exploded side view illustrating the various components of connector 200. The embodiment of connector 200 shown herein includes valve housing 201, valve cap 202, valve plug 207, valve insert 208, and diaphragm 209. As described with respect to FIGS. 1 and 2, valve cap 202 has inlet port 203 with threads 205 that receive an actuator from a fluid dispensing or other device. Internal chamber 222 is formed by valve cap 202 and valve housing 201 when mated together and is designed to receive valve plug 207.

Valve plug 207 is of a generally cylindrical shape for slidably fitting within internal chamber 222 formed by valve cap 202 and valve housing 201. Valve plug includes a primary shoulder seal 219 adapted for abutting against the valve seat 220 of the valve cap 202. Valve plug 14 also includes wiping seal 218 that engages the internal surface of the throat 217 of valve cap 202. As will be described below, wiping seal 218 acts to remove any fluid from the throat 217 of valve cap 202 when an actuator is disengaged from connector 200. Valve plug 207 may also include notch 216. Notch 216 facilitates the deformation of valve plug 207 when under pressure from a Luer actuator. The deformation of valve plug 207 creates a fluid path through connector 200.

Preferred embodiments of connector 200 also include valve insert 208 and diaphragm 209. Valve insert 208 includes bowl 211. When diaphragm 209 is mated with valve insert 208 an air pocket formed in bowl 211. The air pocket in bowl 211 provides a counter pressure to diaphragm 209 during fluid flow and works to ensure a negative fluid displacement during insertion and a positive fluid displacement during disconnection as will be explained. Support ribs 214 provide structural rigidity to valve insert 208 and help support diaphragm 209 within the air pocket of bowl 211 when the diaphragm in an extended or stretched position.

Valve insert 208 and diaphragm 209 perform several functions in connector 200. First, they occupy space that would otherwise be filled by fluid, thereby minimizing the priming volume required to achieve fluid flow through connector 200. Second, they provide the mechanism by which connector 200 achieves the proper fluid flow characteristics, namely positive fluid displacement during disconnection. Further, diaphragm 209 deforms under back pressure in the system, deforming to accept fluid inserted into the connector during back pressure and then positively displacing that fluid out of the connector when the back pressure has subsided. Bowl 211 also provides a volume for valve plug 207 to displace into when valve plug 207 is displaced by an actuator inserted into inlet port 203. Diaphragm 209 stretches into bowl 211 under the force of valve plug 207, but only to the extent necessary, thereby minimizing priming volume. Diaphragm 209 also provide a counter force against valve plug 207, helping to push valve plug 207 back into chamber 222 when the actuator is removed, thereby resealing inlet port 203 of connector 200.

Stem 215 of valve insert 208 extends into outlet port 223 of valve housing 201 further decreasing the internal volume of connector 200 and thereby minimizing the priming volume for fluids flowing through connector 200. Valve insert 208 slides tightly into valve housing 201 creating a tight connection between the external walls of valve insert 208 and the internal walls of valve housing 201. A single flow channel is formed in one of the ribs 206 on the internal side wall of valve housing 201 and also in the base wall of housing 201. Stem 215 is sized such that when inserted into the outlet port 223 of connector 200, the cross sectional flow volume of outlet port 223 will be equivalent to the flow volume through the channel in the side wall of valve housing 201.

Valve housing 201 also includes male Luer 204 and female threads 224. The connection creatable by male Luer 204 and threads 224 is a standardized connection common to medical fluid delivery devices and is the counterpart to the connection formed by the inlet port 203 and male threads 205.

Figure 4:
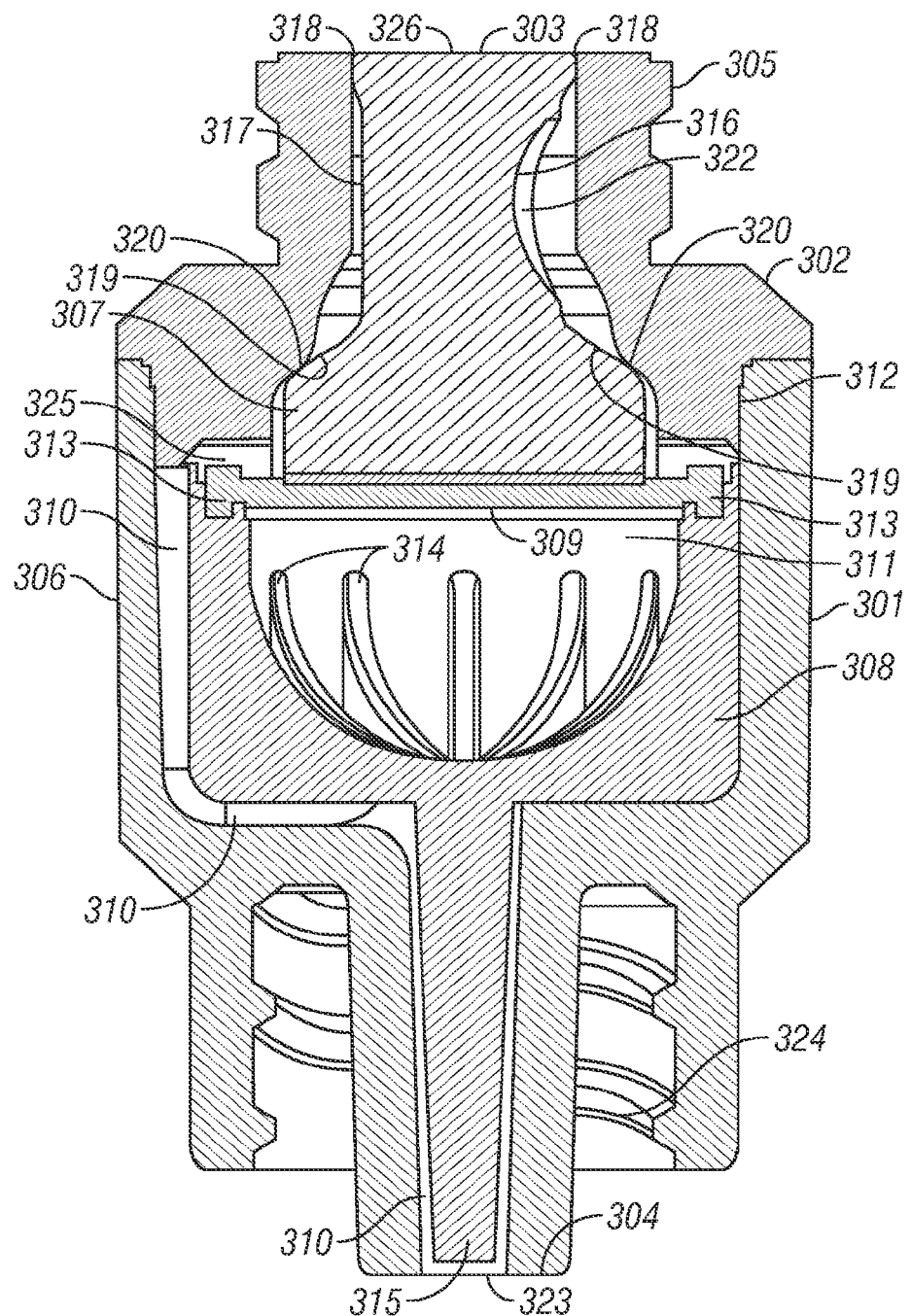
FIG. 4 is a section view of the medical connector shown in FIG. 2.

Referring now to FIG. 4, a cross-section of an embodiment of connector according to the concepts described herein is shown assembled. A preferred embodiment of connector 300 again includes valve housing 301, valve cap 302, valve insert 308, valve plug 307 and diaphragm 309. Valve insert 308 and diaphragm 309 fit tightly into valve housing 301 and held in place by valve cap 302 that is securely attached to valve housing 301 by welding or other means. A flange 313 on diaphragm 309 fits into a groove 312 created by valve cap 302 and valve insert 308.

Flange 313 and groove 312 hold diaphragm 309 securely in place and prevent diaphragm 309 from moving when it deforms into bowl 311.

Valve plug 307 fits into chamber 322 formed when valve cap 302 is fitted to valve housing 301 with valve insert 308 and diaphragm 309 inserted. In the closed position shown, shoulder seal 319 of valve plug 307 abuts tightly against the valve seat 320, preventing any fluid flow through connector 300. Additionally, wiping seal 318 seals the entrance to inlet port 303 by providing a seal around the internal wall of throat 317 of valve cap 302. Wiping seal 318 also acts to remove any fluid from the throat 317 by forcing any fluid in throat 317 up and out of connector 300 when valve plug 307 transitions from an open position to the closed position shown in FIG. 4. Notch 316 of valve plug 307 is used to control the deformation of valve plug 307 under pressure from an actuator (not shown) inserted into connector 300.

Though the connector 300 is shown in the closed position in FIG. 4 with the top portion of the fluid path closed by wiping seal 318 and particularly by shoulder seal 319, the lower portion of the fluid path 310 through connector 300 is shown. Fluid path 310 includes chamber 325 formed by open portion of valve cap 302 and diaphragm 309. Chamber 325 is in communication with the channel impeded in one of the ribs 306 of valve housing 301. While connector 300 is shown with a single channel fluid path, channels in other ribs of valve housing 301 may be used in connector 300 to increase flow volume. Also the size of the channel for fluid path 310 can be altered to alter the flow characteristics of the device. It should be noted that increasing channel size or adding additional channels could increase the priming volume of the device.

The fluid path 310 continues from the channel in rib 306 into a channel in the base of valve housing 301. The fluid path then enters outlet port 323 in male Luer 304 of valve housing 301. Stem 315 is sized such that the remaining open space in outlet port 323 is matched to the flow characteristics of fluid path 310 through the rest of valve housing 301. As stated, stem 315 occupies space in outlet port 323 that would otherwise be part of the priming volume for connector 300.

Male Luer 304 of valve housing 301 allows connector 300 to be inserted into another device such as a manifold, IV line connector or any other device with a universal type female connector. Threads 324 allow connector 300 to be secured in place when connected via male Luer 304. As described, top surface 326 of valve plug 307 sits flush with the top of valve cap 302, and wiping seal 318 removes fluids from inlet port 303 of connector 300 when the connector is disengaged from another device. This arrangement provides connector 300 with a swabbable inlet surface that can be cleaned and disinfected between uses. Other connector devices that use a slit in a septum allow fluids to collect underneath the septum and are not able to be easily disinfected between uses.

During use the male Luer portion of another device forces valve plug down into connector 300. Diaphragm 309 is deformed into bowl 311 by valve plug 307 and shoulder seal 319 separates from valve seat 320, thereby opening fluid path 310 through connector 300. Notch 316 in valve plug 307 controls the deformation of valve plug 307 and allows it to fold down into connector 300 ensuring that valve plug 307 depresses far enough into connector 300 to allow a good connection with the device being inserted. Diaphragm 309 and the air pocket in bowl 311 provide a positive pressure on valve plug 307, thereby ensuring that valve plug 307 reseats properly upon removal of the actuating device.

Further, upon actuation the depression of valve plug 307 on diaphragm 309 creates a larger open volume inside connector 300 thereby drawing downstream fluid into connector 300 providing the desired negative displacement on connection. The return of the valve plug 307 and diaphragm 309 back into the unextended position after disconnection reduces the internal volume of connector 300. As shoulder seal 319 of valve plug 307 prevents fluid from being pushed out of inlet port 303, the fluid in bowl 311 is pushed out of outlet port 323 upon removal of the actuating device, thereby providing the desired positive displacement on disconnection.

With the internal volume of connector 300 being occupied by valve insert 308, diaphragm 309 and valve plug 307, it can be easily seen that the internal volume, which is also the priming volume of connector 300, is minimized. Minimizing priming volume can be important in a variety of applications, but can be particularly important in applications involving low dose medications or in neonatal applications where very low flow rates are maintained. In preferred embodiments of a connector according to the concepts described herein, a low priming volume could be considered a priming volume of 70 microliters or less, though greater priming volumes may be appropriate for other applications while remaining within scope of the concepts described herein.

Referring now to FIGS. 5A through 5D, various aspects of a preferred embodiment of a connector 400 are described. Each of the connectors shown includes a valve housing 401, a valve cap 402, a valve plug 407, a valve insert 408 and a diaphragm 409 as described with respect to FIGS. 1 through 4.

Figure 5A:
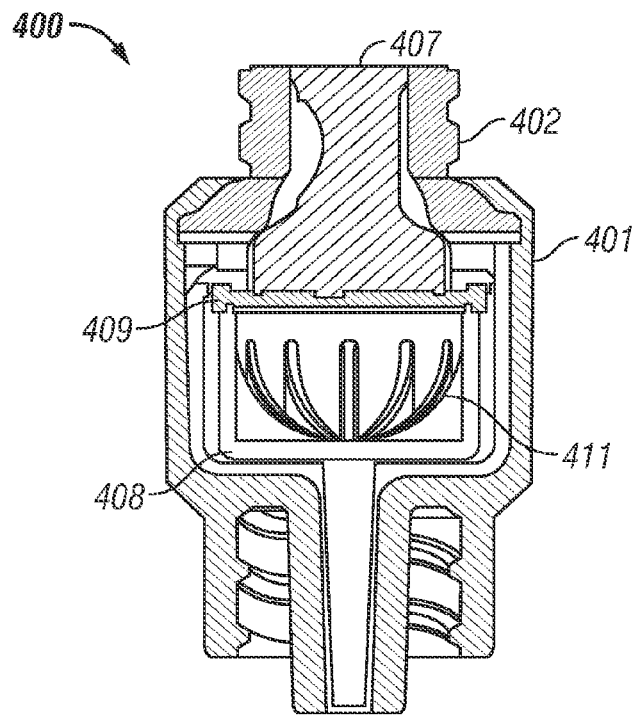
FIGS. 5A-5D are side views of the medical connector shown in FIG. 2, shown in various operational states.
Figure 5B:
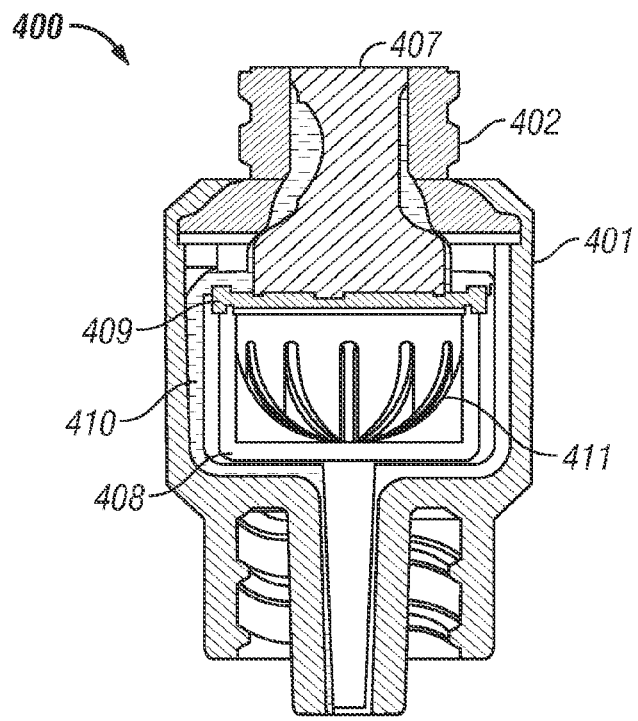

FIG. 5A shows connector 400 in its closed position with valve plug 407 sealing connector 400 and preventing any fluid from passing through the connector 400. Diaphragm 409 is in its normal condition for a closed configuration. FIG. 5B illustrates the portion of fluid path 410 after valve plug 407. As valve plug 407 is in its closed position the fluid path 410 is closed by the valve plug 407 as described with respect to FIG. 4.

Figure 5C:
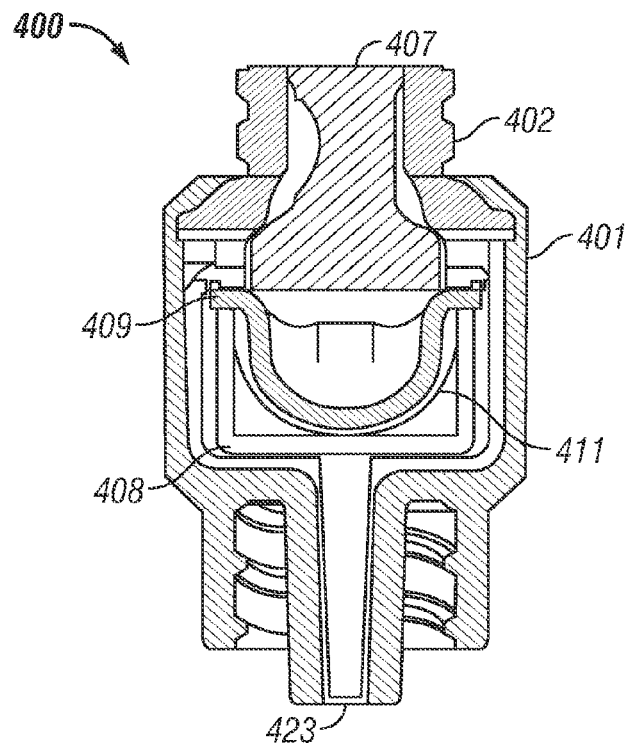

FIG. 5C shows connector 400 under back pressure through outlet port 423. Fluid entering outlet port 423 travels along fluid path 410 shown in FIG. 5B and is blocked by valve plug 407 from exiting connector 400. Instead the fluid causes diaphragm 409 to expand into bowl 411 creating a space for a volume of fluid between valve plug 407 and diaphragm 409. Additionally, valve plug 407 is held in place by the back pressure, thereby reinforcing the seals between valve plug 407 and valve cap 402 and ensuring that connector 400 does not leak under back pressure conditions. When the back pressure condition ends, the elasticity of diaphragm 409 and the pressure from the air pocket in bowl 411 force the fluid that entered the connector under back pressure to exit through outlet port 423.

Figure 5D:
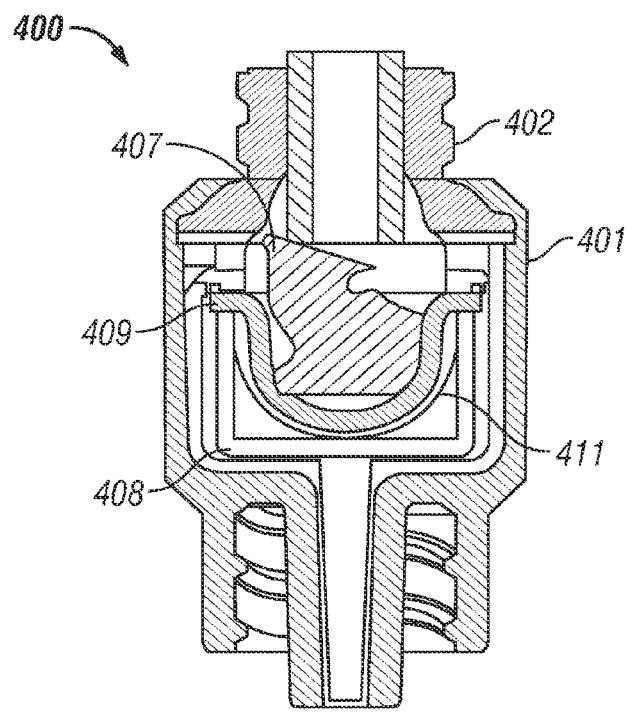

FIG. 5D shows connector 400 in an open or actuated state with a male Luer compressing valve plug 407 into the body of connector 400. Valve plug 407 causes diaphragm 409 to expand into bowl 411 creating space for valve plug 407 and opening the fluid path through the device. Diaphragm 409 and the mass of valve plug 407 minimize the volume inside connector 400 in the actuated state, thereby minimizing the priming volume required by connector 400.

Referring now to FIGS. 6A through 6D, various alternative embodiments of the valve plug and diaphragm in a connector are described. Each of the connectors shown operates essentially as described with respect to FIGS. 1 through 5.

Figure 6A:
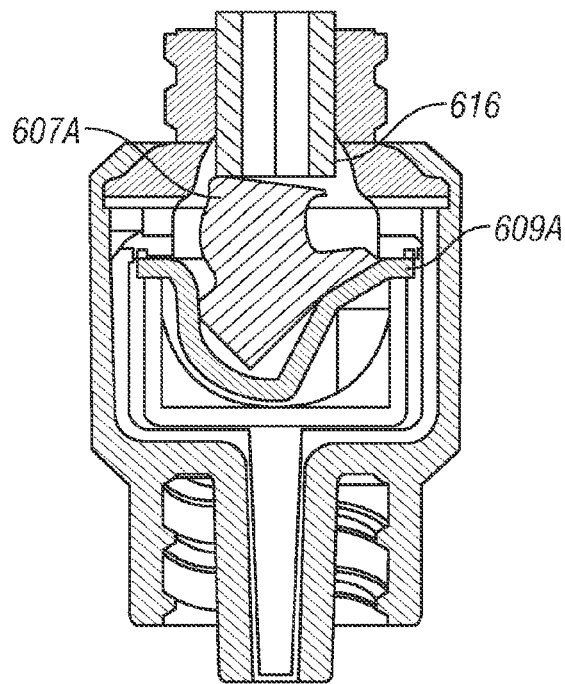
FIGS. 6A-6D are side views of the medical connector shown in FIG. 2, illustrating examples of various alternate embodiments.
Figure 6B:
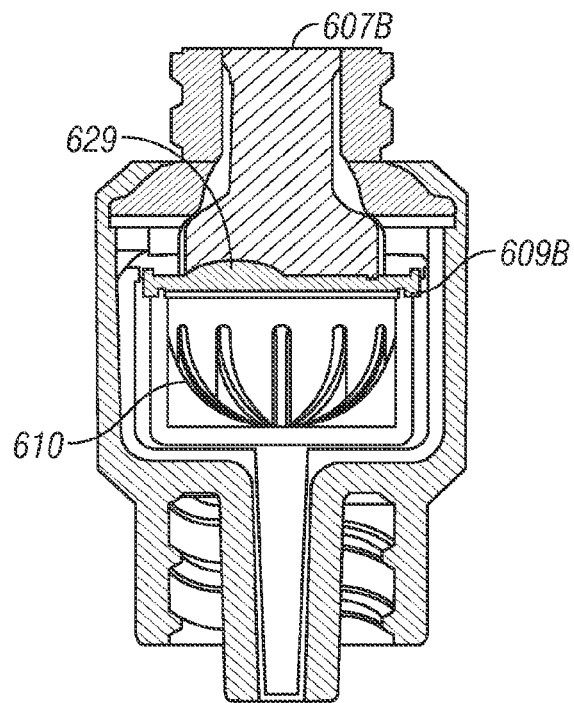

FIG. 6A shows a notched valve plug 609a in its actuated state with diaphragm 609a in its expanded state as described above. The notch allows valve plug 607a to deform in a desired manner upon actuation by a male Luer. FIG. 6B shows a diaphragm 609b having a dimple 630 and a corresponding recess 629 in valve plug 607b. The dimple and recess allow diaphragm 609b and valve plug 607b to deform in a desired manner.

Figure 6C:
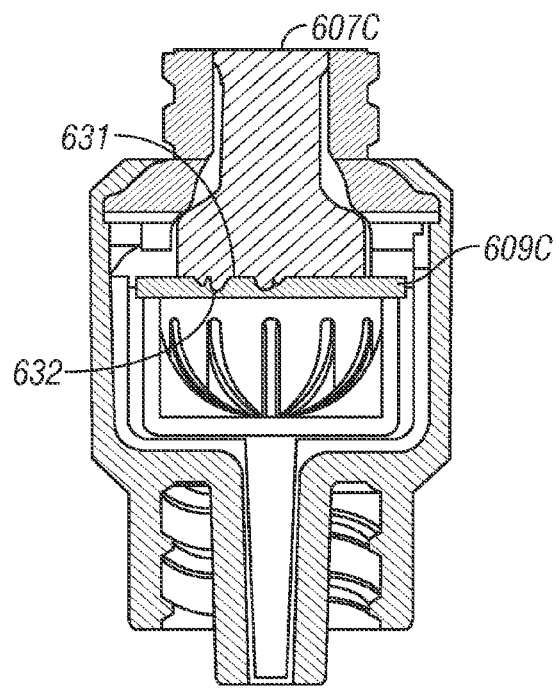
Figure 6D:
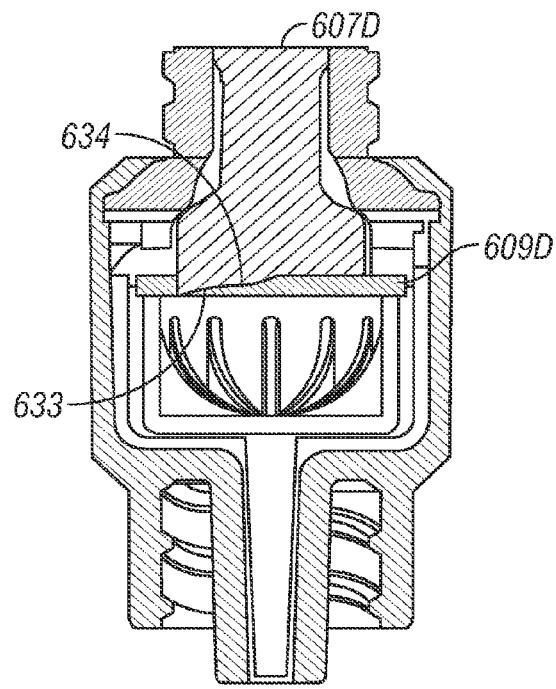

FIG. 6C shows a diaphragm 609c having a recess 632 and a corresponding dimple 631 in valve plug 607c. As before, the dimple and recess allow diaphragm 609c and valve plug 607c to deform in a desired manner. FIG. 6D shows a diaphragm 609d having a notch 633 and a corresponding slant 634 in valve plug 607d. The slant and notch allow diaphragm 609d and valve plug 607d to deform in a desired manner. While certain alternate embodiments have been explicitly shown, one skilled in the art would understand that many other alternate embodiments could be envisioned that would have the same or similar function and still be well within the scope of the concepts described herein.

Figure 7A:
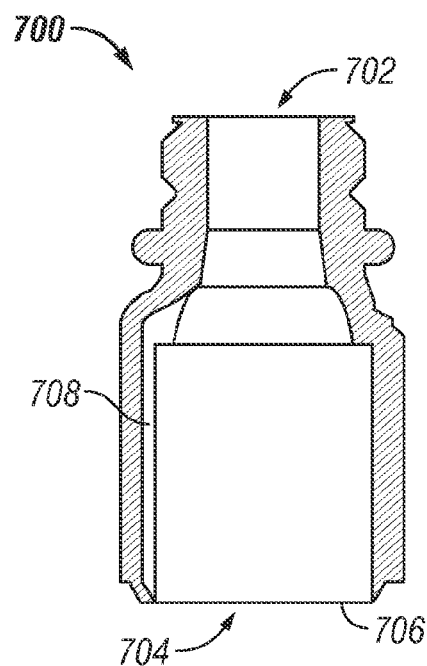
FIGS. 7A-7D are cross-sections of the components of a medical connector according to certain aspects of the disclosure.

FIGS. 7A-7D are cross-sections of the components of a medical connector according to certain aspects of the disclosure. FIG. 7A is the upper shell 700 with an inlet 702 configured to accept, in this embodiment, a male Luer connector 800 shown in FIGS. 8 and 9. There is an internal cavity 704 with a ridge 706 surrounding the opening of internal cavity 704. Ridge 706 is an "energy director" that guides the ultrasonic energy used to fuse the upper shell 700 to the inner pocket 704 during assembly, as described in more detail with reference to FIG. 7E. Inlet 702 is connected to the internal cavity 704. There is at least one channel 708 formed in the interior wall of the outer shell 700 that is discussed in more detail relative to FIG. 7E.

Figure 7B:
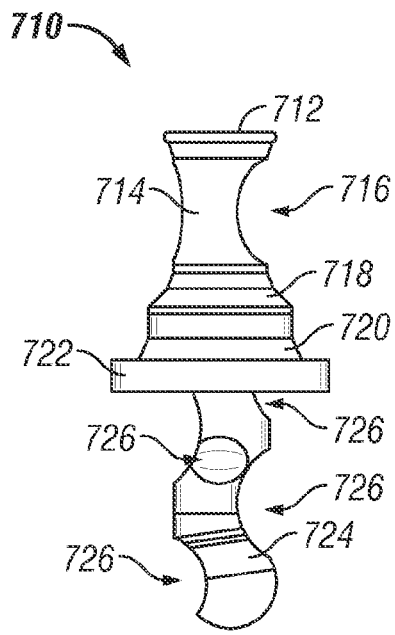

FIG. 7B is a plug 710 that has a face 712 that is sized to fit into the opening 702 and is smooth so as to avoid crevices and corners that might harbor bacteria and be difficult to disinfect. Below the face 712 is a neck 714 having, in this embodiment, one notch 716 that causes the neck 714 to bend preferentially in the direction of the notch 716 when compressed. Below the neck is a shoulder 718 that is connected to a diaphragm 720 that is connected to a sealing ring 722. Below the sealing ring 722 is a biasing element 724 that, in this embodiment, has four notches 726 that cause the biasing element 724 to bend preferentially into a serpentine configuration when compressed. In certain embodiments, there are fewer than four notches 726. The biasing element 724 is attached to shoulder 718 inside the diaphragm 720 as is seen in the cross-section of FIG. 7E.

Figure 7C:
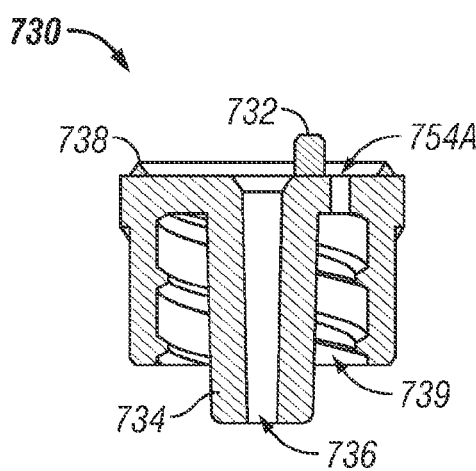

FIG. 7C depicts the base 730 with an outlet 736 within a fitting 734 that, in this configuration, is a male Luer connector. A threaded cavity 739 surrounds the male Luer connector 734. The upper surface of base 730 has a ridge 738 is an "energy director" that guides the ultrasonic energy used to fuse the base 730 to the inner pocket 704 during assembly, as described in more detail with reference to FIG. 7E. There is a vent channel 754A from the upper surface 738 to the threaded cavity 739. There are, in this embodiment, two locating pins 732 that are discussed in more detail relative to FIG. 7D.

Figure 7D:
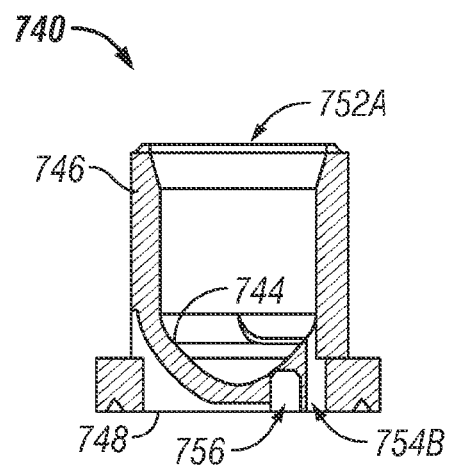

FIG. 7D is the inner pocket 740 with an internal cavity 752A, i.e. a bowl, with a bottom 744 and is surrounded at the open end by a shoulder 746. A vent path 754B connects the internal cavity 752A to the lower surface 748. In this embodiment, two locating pockets 756 are provided that are configured to accept the locating pins 732 of the base 730. The interaction of the pins 732 and locating sockets 756 is discussed in more detail with respect to FIG. 7E.

Figure 7E:
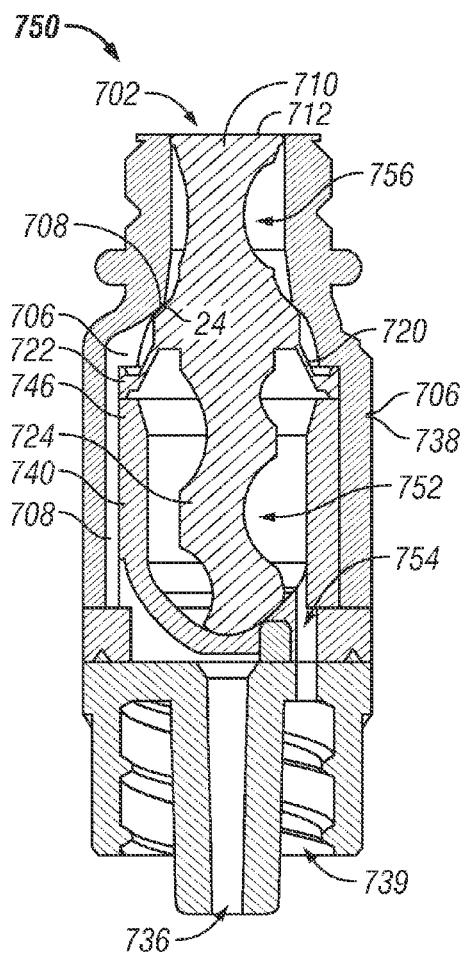
FIG. 7E is a cross-section of the assembled medical connector according to certain aspects of the disclosure.

FIG. 7E is a cross-section of the assembled medical connector 750 according to certain aspects of the disclosure. The connector 750 is assembled by placing the plug 710 into the upper shell 700. The neck 714 of the plug 710 is located within the internal cavity 704 such that the face 712 is flush with and sealed to the opening 702. The inner pocket 740 is then inserted into the upper shell 700 over the plug 710 until the ridge 706 is in contact with the inner pocket 740, whereupon the inner pocket 740 is, in this embodiment, ultrasonically welded to the upper shell 700. The outer circumferential surface of inner pocket 740 is a pressfit with the inner circumferential surface of cavity 704 and forms a fluid-tight flow channel over the channel 708 that is formed in the wall of the cavity 704. The base 730 is then attached to the inner pocket 740 by aligning the alignment pins 732 with the alignment sockets 756 and then bringing the ridge 738 of the base 730 into contact with the lower surface 748 of the inner pocket 740. In this embodiment, the base 730 is ultrasonically welded to the inner pocket 740. In this configuration, the vent paths 754A and 754B are aligned and form a continuous vent path 754 from the internal cavity 752A to the threaded cavity 739.

When fully assembled, the sealing ring 722 of plug 710 is compressed between the upper shell 700 and the shoulder 746 of the inner pocket 740. The diaphragm 720 and the walls of the inner pocket 740 form a sealed internal cavity 752 with a vent path 754 to the ambient environment through the threaded cavity 739. A second internal cavity 758 is formed by the diaphragm 720 and the inner wall of the upper shell 700 and the sealed perimeter of face 712 of the plug 710. The channel 708 formed between the inner wall of the upper shell 700 and the outer wall of the inner pocket 740 forms a fluid path from the internal cavity 758 to the outlet 736. The operation and function of the two internal cavities 752, 758 are discussed in more detail with respect to FIGS. 8 and 9.

Figure 8:
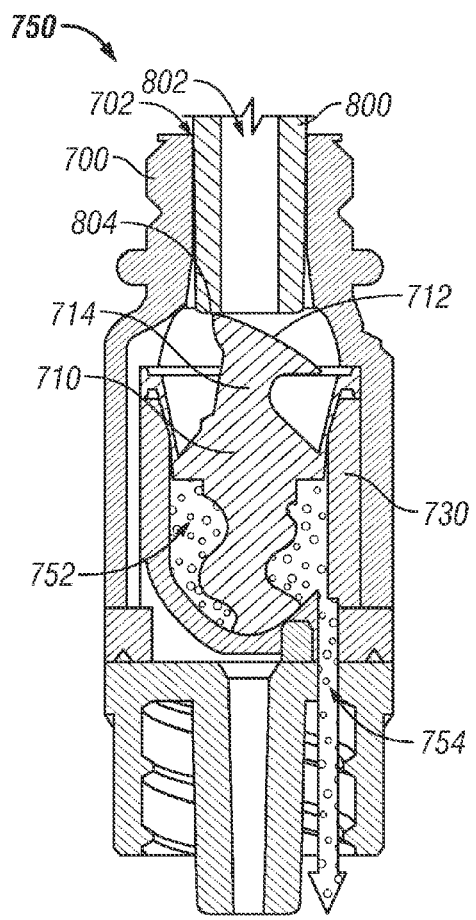
FIG. 8 depicts the air space and vent path of the medical connector of FIG. 7E according to certain aspects of the disclosure.

FIG. 8 depicts the air space 752 and vent path 754 of the medical connector 750 of FIG. 7E according to certain aspects of the disclosure. In this view, the connector 750 has been actuated by insertion of a mating connector element that, in this embodiment, is a male Luer connector 800. The connector 800 has a central lumen 802 and a tip 804. As the connector 800 enters the inlet 702 of housing 700, the tip 804 contacts plug face 712 and displaces the plug 710 in the distal direction. When connector 800 is fully inserted, neck 714 deflects according to the notch 716 such that the plug face 712 tilts away from the tip 804, as can be seen in FIG. 8. The deflection of the plug 710 stretches the diaphragm 720 as the neck 714 descends into the internal cavity 752. As the internal cavity 752 remains sealed by the diaphragm 720, the air in the internal cavity 752 escapes through the vent path 754.

Figure 9:
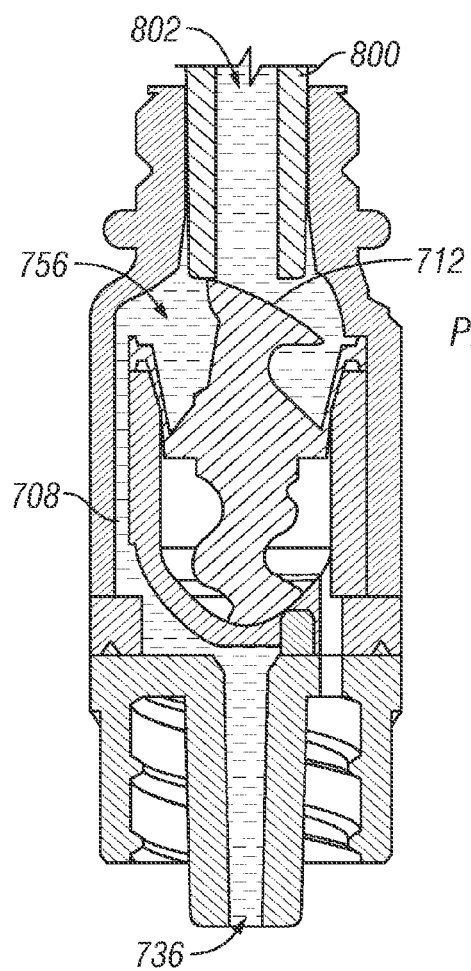
FIG. 9 depicts the liquid flow path of the medical connector of FIG. 7E according to certain aspects of the disclosure.

FIG. 9 depicts the liquid flow path of the medical connector of FIG. 7E according to certain aspects of the disclosure. The configuration of connector 750 in FIG. 9 is identical to the configuration shown in FIG. 8. In FIG. 9, the second internal cavity 758 has been filled with liquid entering from connector 800 through lumen 802. As can be seen in FIG. 9, with the connector 800 in place, there is a fluid path from lumen 802 past the tilted face 712 and through the internal cavity 758 along the channel 708 to the outlet 736 such that fluid may flow through the mated connectors 750, 800.

Figure 10:
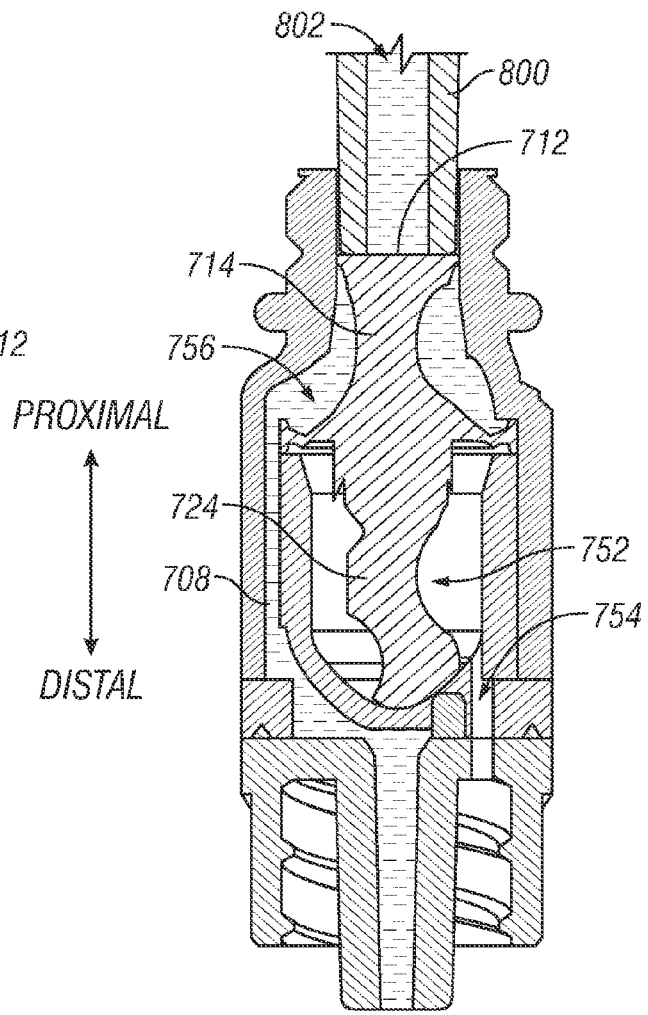
FIG. 10 depicts the connector as the connector is partially demated according to certain aspects of the disclosure.

FIG. 10 depicts the connector 750 as the connector 800 is partially demated according to certain aspects of the disclosure. As the connector 800 is withdrawn from the connector 750, the elastic nature of diaphragm 720 and the biasing element 724 both push the plug 710 upwards and maintain contact between the tip 804 and the face 712. The volume of the internal cavity 758 has decreased compared to the volume of the fully mated configuration of FIG. 9. Neck 714 has rotated as the displacement of plug 710 is reduced and the face 712 is now sealing across the tip 804 and blocking flow through the lumen 802. As the volume of internal cavity 758 decreases, fluid from internal cavity 758 flows through the channel 708 and out through outlet 736. This is the "positive displacement" function of connector 750, wherein fluid is forced toward the patient, i.e. out through outlet 736, upon disconnection of the connector 800 from connector 750. The benefit of positive displacement is that it prevents retrograde flow, i.e. drawing blood from the patient into the IV tubing (not shown) toward the connector 750. When blood is drawn into the IV tubing and not immediately flushed back into the patient, there is a risk that the blood may coagulate and block the IV tubing, requiring either manual flushing or replacement of the IV set. As the internal cavity 76 contracts and expels the fluid, internal cavity 752 expands and draws air in through the vent path 754.

Figure 11:
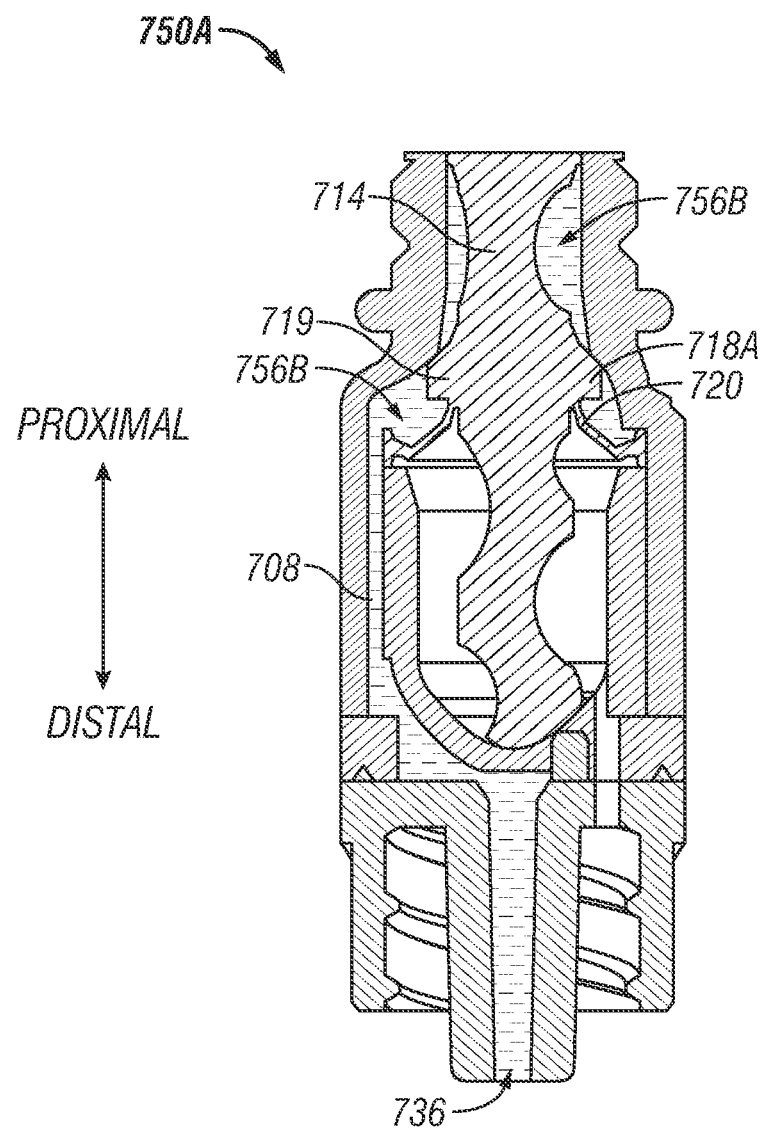
FIG. 11 depicts a connector that includes another embodiment of the plug according to certain aspects of the disclosure.

FIG. 11 depicts a connector 750A that includes another embodiment of the plug 710A according to certain aspects of the disclosure. In this embodiment, the shoulder 718A protrudes out and overhangs the diaphragm 720. The shoulder 718A contacts the outer shell 700 and separates internal cavity 758 into a first volume 758A above the shoulder 718A and a second volume 758B below the shoulder 718A. There is a slit 719 between the underside and the top edge of the shoulder 718A that passes by the point of contact between the shoulder 718A and the upper shell 700. In the case of back pressure introduced through outlet 736 when the connector 750A is not activated, pressure will build up in internal volume 758B. A positive pressure differential between internal volume 758B and 758A causes the slit 719 will open up, thereby allowing the pressure of internal cavity 758A to increase to the pressure of internal volume 758B. Pressure in internal volume 758A is applied upward on the neck 714 of the plug 710 to create a tighter seal between the face 712 and the inlet 702 of the upper shell 700 and prevent leakage from inlet 702.

In summary, the disclosed connector provides a swabbable surface on the exposed face of the unmated connector such that the interface may be sterilized prior to mating of the connector halves. The connector is self-sealing such that liquid does not drip from the connector after demating. The connector also, in certain embodiments, positively displaces fluid during the demating process to avoid retrograde flow. In certain embodiments, the connector has a near-zero displacement such that fluid is neither expelled from nor drawn into the connector during the demating process.

The previous description is provided to enable a person of ordinary skill in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

The term "slit" refers to any passage through an object, including a single planar separation as well as passages having other cross-section profiles such as an "X." The passages may be closed in one configuration and open in a second configuration.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A connector comprising:
  a housing having an internal cavity with a first port, a second port, and a fluid path from the first port through the internal cavity to the second port; and
  a plug having a first position and a second position within the internal cavity, the plug configured to block the fluid path between the first port and the internal cavity when in the first position, the plug comprising:
    a diaphragm configured to separate the internal cavity into a first volume that is vented and a second volume that includes the fluid path;
    a biasing element disposed within the first volume, the biasing element configured to urge the plug toward the first position;
    a shoulder that contacts the housing and separates the second volume into a third volume between the first port and the shoulder and a fourth volume between the shoulder and the second port; and
    a passage from the fourth volume through the plug to the third volume, wherein the passage is open when a pressure in the fourth volume is greater than a pressure in the third volume and the passage is closed when the pressure in the fourth volume is not greater than the pressure in the third volume,
  wherein displacement of the plug from the first position toward the second position opens the fluid path and increases the second volume.

2. The connector of claim 1, wherein a fluid is drawn into the second volume through the second port when the plug moves toward the second position.

3. The connector of claim 2, wherein the fluid is expelled from the second volume through the second port when the plug moves toward the first position.

4. The connector of claim 2, wherein the plug has a smooth surface that is flush with the first port when the plug is in the first position.

5. The connector of claim 2, wherein the second volume is less than 70 microliters.

6. The connector of claim 2, wherein the biasing element has at least one notch configured to cause the biasing element to controllably deform when the plug is compressed.

7. The connector of claim 6, wherein the biasing element has a plurality of notches configured to cause the biasing element to controllably deform in a serpentine shape when the plug is compressed.

8. The connector of claim 1, wherein the first port is configured as a female Luer connector.

9. The connector of claim 1, wherein the second port is configured as a male Luer connector.

* * * * *